United States Patent [19]
Shiu

[11] Patent Number: 5,423,799
[45] Date of Patent: Jun. 13, 1995

[54] SURGICAL INSTRUMENT

[75] Inventor: Man F. Shiu, Birmingham, United Kingdom

[73] Assignee: Medtronic, Inc., Minneapolis, Minn.

[21] Appl. No.: 10,505

[22] Filed: Jan. 28, 1993

Related U.S. Application Data

[63] Continuation of Ser. No. 900,555, Jun. 18, 1992, abandoned, which is a continuation of Ser. No. 789,779, Nov. 8, 1991, abandoned, which is a continuation of Ser. No. 450,130, Dec. 13, 1989, abandoned.

[30] Foreign Application Priority Data

Dec. 14, 1988 [GB] United Kingdom ............... 8829182

[51] Int. Cl.$^6$ ............................................. H61B 17/32
[52] U.S. Cl. ................................... 606/159; 606/170
[58] Field of Search .................. 604/22; 606/159, 170, 606/171

[56] References Cited

U.S. PATENT DOCUMENTS

| | | | |
|---|---|---|---|
| 2,701,559 | 2/1955 | Cooper | 128/2 |
| 2,850,007 | 2/1958 | Lingley | 128/2 |
| 3,064,651 | 11/1962 | Henderson | 128/221 |
| 3,082,805 | 3/1963 | Royce | 146/68 |
| 3,614,953 | 10/1971 | Moss | 606/159 |
| 3,683,891 | 8/1972 | Eskridge et al. | 128/2 B |
| 3,732,858 | 5/1973 | Banko | 128/2 B |
| 3,749,085 | 7/1973 | Willson et al. | 128/2 B |
| 3,800,783 | 4/1974 | Jamshidi | 128/2 B |
| 3,937,222 | 2/1976 | Banko | 606/170 |
| 3,945,375 | 3/1976 | Banko | 128/6 |
| 3,976,077 | 8/1976 | Kerfoot, Jr. | 128/305 |
| 4,007,732 | 2/1977 | Kvavle et al. | 128/2 B |
| 4,030,503 | 6/1977 | Clark, III . | |
| 4,177,797 | 12/1979 | Baylis et al. | 128/754 |
| 4,273,128 | 6/1981 | Lary | 128/305 |
| 4,368,730 | 1/1983 | Sharrock | 604/158 |
| 4,490,139 | 12/1984 | Huizenga et al. | 604/57 |
| 4,512,344 | 4/1985 | Barber | 128/305 |
| 4,603,694 | 8/1986 | Wheeler | 128/312 |
| 4,646,719 | 3/1987 | Neuman et al. | 128/1 D |
| 4,646,736 | 3/1987 | Auth | 128/303 |
| 4,646,738 | 3/1987 | Trott | 128/305 |
| 4,653,496 | 3/1987 | Bundy et al. | 128/305 |
| 4,669,469 | 6/1987 | Gifford, III et al. | 128/305 |
| 4,679,558 | 7/1987 | Kensey et al. | 606/180 |
| 4,686,982 | 8/1987 | Nash | 128/305 |
| 4,695,667 | 9/1987 | Masch | 604/22 |
| 4,706,671 | 11/1987 | Weinrib | 128/348.1 |
| 4,732,154 | 3/1988 | Shiber . | |
| 4,745,919 | 5/1988 | Bundy et al. | 606/159 |
| 4,754,755 | 7/1988 | Husted . | |
| 4,765,332 | 8/1988 | Fischell et al. | 128/305 |
| 4,771,774 | 9/1988 | Simpson et al. | 128/305 |
| 4,781,186 | 11/1988 | Simpson et al. | 128/305 |
| 4,784,636 | 11/1988 | Rydell | 604/22 |

(List continued on next page.)

FOREIGN PATENT DOCUMENTS

| | | | |
|---|---|---|---|
| 0086048 | 8/1983 | European Pat. Off. . | |
| 0291170 | 11/1988 | European Pat. Off. . | |
| 2093353 | 9/1982 | United Kingdom . | |
| 442795 | 9/1974 | U.S.S.R. | 606/159 |
| 665908 | 6/1979 | U.S.S.R. | 606/159 |
| 8906517 | 7/1989 | WIPO . | |

Primary Examiner—Jerome L. Kruter
Attorney, Agent, or Firm—Dianne M. F. Plunkett; Harold R. Patton

[57] ABSTRACT

A medical device for removing material from a body vessel comprising a tube, a drive shaft extending through the tube, a stepped root mounted to the drive shaft, a rotatable screw having a distal and proximal end, the screw extending outward from the stepped root to form a helix with an edge, the rotatable screw having a tip and sharp outer cutting edges having a tapered diameter along its length to a minimum diameter at its distal end, and a generally cylindrical housing enclosing the sharp edge of the screw so that the tip of the screw extends outside the housing and enters the tissue, and the sharp edge, in cooperation with the housing, cuts the tissue. The housing has a leading inner edge so that the tissue is removed from the vessel as it enters the housing by cooperation of the screw and the leading inner edge.

6 Claims, 3 Drawing Sheets

U.S. PATENT DOCUMENTS

| | | | |
|---|---|---|---|
| 4,794,931 | 1/1989 | Yock | 128/660.03 |
| 4,819,634 | 4/1989 | Shiber | 128/305 |
| 4,842,579 | 6/1989 | Shiber | 604/22 |
| 4,844,064 | 7/1989 | Thimsen et al. | 128/305 |
| 4,850,957 | 7/1989 | Summers | 604/22 |
| 4,883,458 | 11/1989 | Shiber . | |
| 4,886,490 | 12/1989 | Shiber . | |
| 4,894,051 | 1/1990 | Shiber . | |
| 4,926,858 | 5/1990 | Gifford et al. | 606/170 |
| 4,957,482 | 9/1990 | Shiber . | |
| 4,979,939 | 12/1990 | Shiber . | |
| 5,002,553 | 3/1991 | Shiber . | |
| 5,007,896 | 4/1991 | Shiber . | |

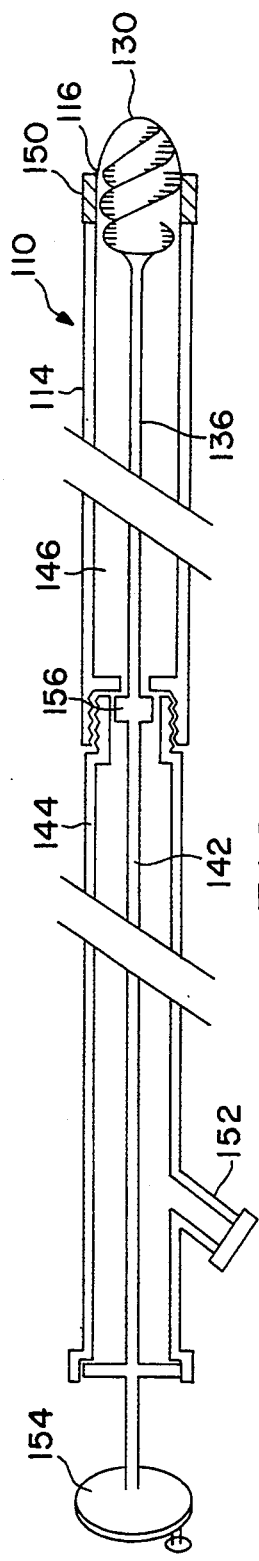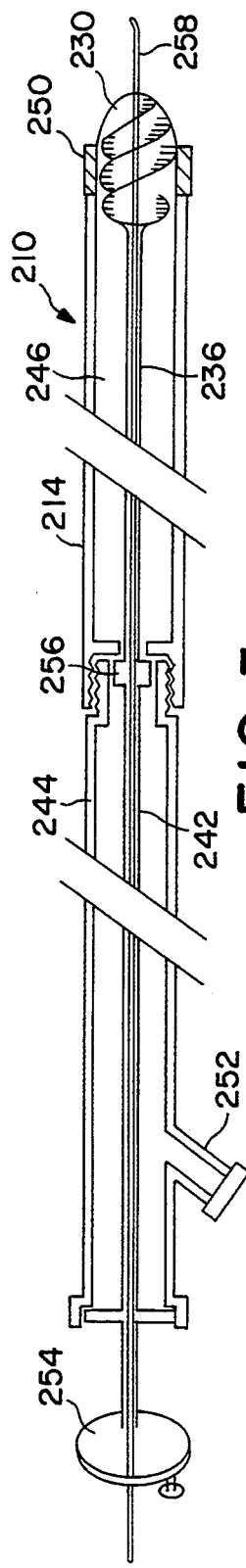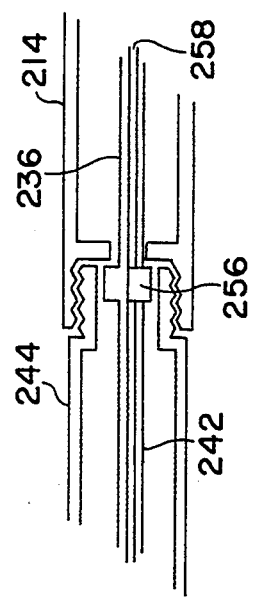

SURGICAL INSTRUMENT

This is a continuation of application Ser. No. 07/900,555, filed Jun. 18, 1992, now abandoned which is a continuation of application Ser. No. 07/789,779, filed Nov. 8, 1991, now abandoned which is a continuation of Ser. No. 07/450,130, filed Dec. 13, 1989, now abandoned.

FIELD OF THE INVENTION

This invention relates to a surgical instrument for clearing obstructions in ducts, particularly but not exclusively arteries.

BACKGROUND OF THE INVENTION

A number of techniques are known for clearing obstructions in coronary arteries. These include by-pass surgery, the use of a "balloon" to expand the arterial wall in the region of the obstruction, the use of a cutter passed along the artery to remove the obstruction and the use of a drill which is also passed along the artery to pulverise the obstruction. By-pass surgery is a major operation and is expensive. The use of surgical instruments in the above-described alternative methods involves the risk that the instrument which is passed along the artery will puncture the arterial wall during use or during passage along the artery to the location at which the obstruction is to be cleared. Additionally, the use of a drill which pulverises the obstruction involves the risk of the pulverised material lodging in another part of the body and causing damage there.

It is an object of the present invention to provide a surgical instrument for clearing obstructions in ducts in which the above described problems can be obviated or mitigated.

SUMMARY OF THE INVENTION

According to the present invention, there is provided a surgical instrument for clearing obstructions in ducts, comprising a body having a forward end defined by a sleeve, a cutter member mounted in the sleeve for rotation relative thereto, and elongate flexible drive means connected to the cutter member and extending rearwardly of the body to enable rotation of the cutter member, wherein the cutter member includes an outer cutting edge cooperating with the sleeve to produce a circular cut upon rotation of the cutter member in use.

With the above-described surgical instrument, the sleeve assists in preventing accidental penetration of the wall of the duct by the cutter member during use or when being manoeuvered into position for use. The instrument can be used percutaneously as a non-operative device.

It is preferred for the cutter member to include a blade having a helical outer cutting edge, and particularly preferred for the cutter member to take the form of a screw whose outer surface cooperates with the sleeve to produce the circular cut. Such screw also serves, upon rotation, to transport material from the obstruction into the body of the instrument. Conveniently, a chamber is provided in the body to receive such material which can then be completely removed from the duct upon removal of the body of the instrument therefrom. Thus, the material which has been cleared away is completely removed from the duct.

In a particularly preferred embodiment, the forward end of the cutter member protrudes through the forward open end of the body. To reduce the risk of such cutter member accidentally penetrating the wall of the duct in use or whilst it is being manoeuvred into position along a duct, it is convenient for the forward end of the cutter member to be relatively blunt. However, in the case where the cutter member takes the form of the screw, it is preferred for it to have a tapered forward end protruding from the forward end of the sleeve. Such tapered forward end can then serve to penetrate the obstruction and draw the body along the duct upon rotation of the screw. This is considered to be a particularly effective way of advancing the body along the duct since it does not require the body of the instrument to be pushed along the duct.

The elongate flexible drive means preferably takes the form of a cable or the like mounted for rotary movement within a relatively fixed, flexible sleeve. The flexible sleeve preferably takes the form of a hollow helical spring which is preferably provided with a continuous cover or sheath to provide a smooth external surface for ease of passage along the duct to be cleared.

The body and the cutter member may be provided with a passage extending axially therethrough so that the body and the cutter can be mounted on an elongate guide wire or the like. In use, it will be appreciated that such guide wire can be passed along the duct relatively easily because of its small diameter, and then the body can be passed along the duct whilst being guided by the wire so as to facilitate safe passage along the duct to the site of the obstruction. The surgical instrument will normally be used whilst the patient is conscious, and its progress along the duct can be monitored by x-ray inspection.

In the case of surgical instruments according to the present invention designed for clearing arterial obstructions, the external diameter of the body will be in the region of 2 to 4 mm. The instrument can be used for bioducts generally.

Embodiments of the present invention will now be described, by way of example, with reference to the accompanying drawings, in which:

BRIEF DESCRIPTION OF THE DRAWINGS

FIGS. 2 and 3 are schematic axial sections through parts of second and third examples of surgical instruments according to the present invention;

FIG. 4 is a schematic view illustrating a detail of the instrument of FIG. 3.

DESCRIPTION OF THE PREFERRED EMBODIMENTS

Figure 1:
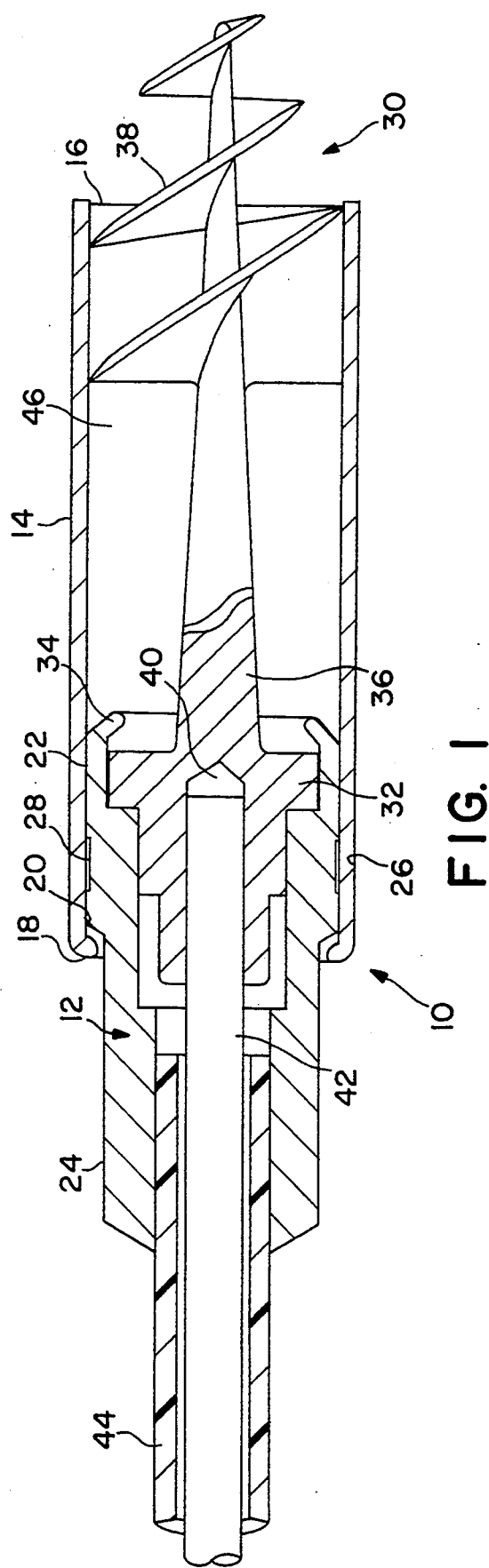
FIG. 1 is an axial section through a first example of surgical instrument according to the present invention.

Referring now to FIG. 1, the surgical instrument illustrated therein is for clearing obstructions in coronary arteries. The instrument comprises a body 10 formed in two parts consisting of a hollow bushing 12 and sleeve 14 extending forwardly of the bushing 12. The sleeve 14 has an open forward end 16 and a rear end which has been inwardly deformed so as to define a stop 18. The stop 18 abuts against a step 20 provided on the external surface of the bushing 12 between a larger diameter forward end portion 22 and a smaller diameter rear end portion 24 thereof. The sleeve 14 is slidable rearwardly (i.e. to the left as viewed in the drawing) relative to the bushing 12 from an extended position in which (a) the stop 18 abuts against step 20 and (b) a pip 26 formed by localised inward deformation of the sleeve 14 engages in an annular groove 28 formed in the surface of the larger diameter forward end portion 22 of the bushing 12. The engagement of the pip 26 in the groove 28 serves as a releasable detent mechanism for retaining the sleeve 14 in its extended condition as illustrated in the drawing.

The surgical instrument further includes a cutter member 30 which is mounted in the body 10 via a stepped root portion 32. The root portion 32 engages in a stepped bore of the bushing 12 and is retained therein by an inwardly upset annular lip 34. The root portion 32 is rotatable relative to the bushing 12 which acts as a bearing therefor. The root portion 32 carries a tapered shaft 36 which projects forwardly and axially of the sleeve 14 so as to pass through the open end 16 of the sleeve 14. At a position which is spaced forwardly of the bushing 12, the shaft 36 is provided with integral screw threading 38 thereon. The screw threading 38 starts within the sleeve 14 and extends forwardly to the tip of the shaft 36, the screw threading tapering inwardly over a region thereof which is disposed externally of the sleeve 14. The forward end of the screw threading 38 and the forward end of the shaft 36 are relatively blunt and have no sharp edges whereby to minimise risk of inadvertent penetration of the arterial wall during use. The portion of the screw threading 38 which is disposed within the sleeve 14 has a peripheral surface which is relatively sharp and which is in close sliding contact with the internal wall surface of the sleeve 14.

The root portion 32 has a blind axial bore 40 therein in which one end of a flexible drive cable 42 is firmly secured. The drive cable 42 extends through a flexible outer sleeve or sheath 44 and is rotatable relative thereto. In the drawing, only a short length of the cable 42 and sheath 44 are illustrated. In practice, these latter two parts will extend for a considerable distance rearwardly of the body 10, with the cable 42 terminating externally of the sheath 44 in a formation which facilitates manual rotation of the cable 42 at a remote location.

In use, the body 10 including the cutter member 30 is passed along an artery of a conscious patient until it meets the obstruction to be cleared. This is effected by appropriately manoeuvering the body 10 using the sheath 44 with the aid of an x-ray camera. When the body 10 has been manoeuvred into the correct position along the artery, the cable 42 is rotated relative to the sheath 44 so as to cause the cutter member 30 to rotate in a direction in which it causes the forward end of the screw threading 38 to dig into the material of the obstruction and thereby draw itself and the body 10 along the artery and further into the obstruction. A circular cutting action is provided by mutual cooperation of (a) the outer cutting edge of that portion of the screw threading 36 which is disposed within the sleeve 14 and (b) the inner peripheral wall of the sleeve 14. The cut material is carried between the flights of the screw threading 38 within the sleeve 14 to be discharged into collection chamber 46 disposed within the sleeve 14 and between the screw threading 38 and the bushing 12. When it is seen on the X-ray camera that the obstruction has been cleared, rotation of the cable 42 is stopped and the body 10 is withdrawn by employing a pulling action on the sheath 44. Once the body 10 has been removed from the artery 10, material which has been collected in the chamber 46 can be easily removed upon retraction of the sleeve 14 relative to the bushing 12.

It will be appreciated that, because the cutting action takes place by cooperation of the screw threading 38 with the internal wall of the sleeve 14, there is a minimum of risk that the wall of the artery will be inadvertently penetrated. In order to assist insertion of the body 10 and to minimise risk of damage to the artery wall, the leading edge of the sleeve 14 around the open end 16 is conveniently radiussed. In order to facilitate withdrawal of the body 10 along the artery, the rear end of the smaller diameter portion 24 of the bushing 12 and the rear edge of the sleeve 14 adjacent the stop 18 are both appropriately tapered.

Referring now to FIG. 2, the surgical instrument illustrated therein is similar to that of FIG. 1 and similar parts are accorded the same reference numerals but in the 100 series. In this example, cutter member 130 is rounded at its forward end to minimise risk of arterial wall penetration in use. Sleeve 114 of body 110 is flexible, but is fitted with a metal ring 150 to define open forward end 116. The rotary cutting action takes place between cutter member 130 and metal ring 150. The body is internally screw-threaded at its rearward end to engage with external screw-threading on the forward end of sheath 144. The screw-threading is directed so that the screw-threaded joint between the body 110 and the sheath 144 tends to be tightened during forward rotation of the cutter member 130 in use. The sheath 144 may have a smaller diameter than the body 110. At its rear end, the sheath 144 is provided with a formation 152 to facilitate gripping of the instrument during use. Cable 142 passes out of the rear end of the sheath 144 and is connected to a hand wheel 154 (only schematically shown). The cable 142 is connected to shaft 136 by connector 156 which also acts as a bearing.

Referring now to FIGS. 3 and 4, the surgical instrument illustrated therein is similar to that of FIG. 2 and similar parts are accorded the same reference numerals but in the 200 series. In this example, cutter member 230 and shaft 236 have aligned axial passages therethrough, and the cable 142 is replaced by a flexible tube 242 which is joined to the shaft 236 at connector 256 which is hollow. These axial passages typically have a diameter of about 0.4–0.46 mm. In use, a guide wire 258 typically having a diameter of about 0.36 mm is passed into and along the artery to a position beyond the location at which the obstruction exists. The body 210 can then be passed along the artery to the location of the obstruction whilst being continually guided by the wire 258 so as to minimise the risk of penetration of or damage to the wall of the artery.

Figure 5:
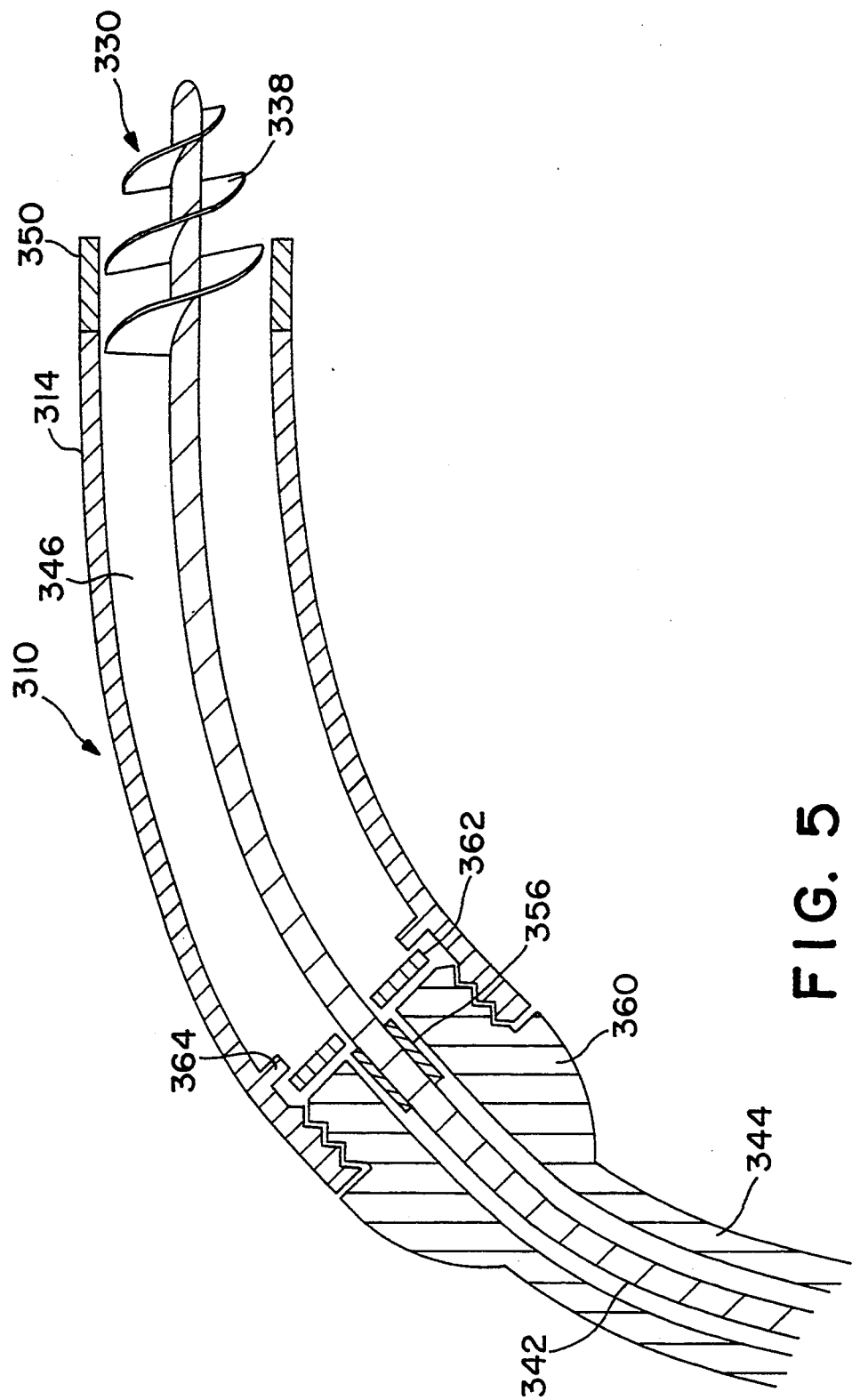
FIG. 5 is an axial section through part of a fourth example of surgical instrument according to the present invention.

Referring now to FIG. 5 of the drawings, the surgical instrument illustrated therein is similar to the preceding examples and similar parts are accorded the same reference numerals but in the 300 series. In this example, sheath 344 has a diameter which is substantially less than that of body 310 except for an enlarged forward end portion 360 by which it is screw-engaged with body 310. A bushing 356 around cable 342 assists in correctly locating the latter within the portion 360. A washer 362 in the body 310 and lodged between the portion 360 and an internal rib 364 serves to limit passage of debris into the sheath 344 from chamber 346 and can be readily removed upon detachment of the body 310 from the portion 360 to facilitate removal of debris from the chamber 346 after use.

I claim:

1. A medical device for removing material from a body vessel comprising:
   a tube;
   a drive shaft extending through the tube;
   a stepped root mounted to the drive shaft;
   a rotatable screw having a distal and proximal end, said screw extending outward from the stepped root to form a helix with an edge, the rotatable screw having a tip and sharp outer cutting edges having a tapering diameter along its length to a minimum diameter at its distal end; and
   a generally cylindrical housing enclosing the sharp edge of the screw so that the tip of the screw extends outside the housing and enters the tissue and the sharp edge in cooperation with the housing cuts the tissue.

2. The device of claim 1 and wherein the housing has a leading inner edge so that tissue is removed from the vessel as it enters the housing by cooperation of the screw with the leading inner edge.

3. A medical device for removing material from a body vessel comprising:
   a tube;
   a drive shaft extending through the tube;
   a stepped root mounted to said drive shaft;
   a rotatable screw having a distal end and a proximal end, said screw attached to the drive shaft and having a tip and sharp edges;
   a generally cylindrical housing enclosing the sharp edge of the screw so that the tip of the screw extends outside the housing and enters the tissue and the sharp edge in cooperation with the housing cuts the tissue; and
   wherein the tip is tapered to facilitate entry of the screw into the tissue to be removed, said tip having a tapering diameter along its length to a minimum diameter at its distal end.

4. A device for cutting tissue from a body vessel comprising:
   a tube;
   a drive shaft extending through the tube;
   a stepped root mounted to the drive shaft;
   a rotatable screw having a distal and proximal end, said screw extending outward from the stepped root to form a helix with an edge, the rotatable screw having a sharp outer cutting edge having a tapering diameter along its length to a minimum diameter at its distal end; and
   a housing for the screw extending around a portion of the screw, the housing having a leading inner edge so that the sharp edges and the leading inner edge cooperate to cut the tissue.

5. A device according to claim 4 and wherein the tip of the screw extends beyond the leading inner edge.

6. A device for cutting tissue from a body vessel comprising:
   a tube;
   a drive shaft extending through the tube;
   a stepped root mounted to said drive shaft;
   a rotatable screw having a distal end and a proximal end, said screw attached to the drive shaft and having a sharp edge; and
   a housing for the screw extending around a portion of the screw, the housing having a leading inner edge so that the sharp edges and the leading inner edge cooperate to cut the tissue and wherein the tip of the screw extends beyond the leading inner edge and wherein the tip is tapered to facilitate entry of the screw into the tissue to be removed, said tip having a tapering diameter along its length to a minimum diameter at its distal end.

* * * * *